(12) United States Patent
Chae et al.

(10) Patent No.: US 11,884,622 B2
(45) Date of Patent: Jan. 30, 2024

(54) TRICYCLODECANE DIMETHANOL COMPOSITION AND PREPARATION METHOD OF THE SAME

(71) Applicant: SK CHEMICALS CO., LTD., Gyeonggi-do (KR)

(72) Inventors: Hee Il Chae, Gyeonggi-do (KR); Ju-Sik Kang, Gyeonggi-do (KR); Jeong Ho Park, Gyeonggi-do (KR); Song Lee, Gyeonggi-do (KR); Yu Mi Chang, Gyeonggi-do (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 0 days.

(21) Appl. No.: 18/003,441

(22) PCT Filed: May 20, 2022

(86) PCT No.: PCT/KR2022/007236
§ 371 (c)(1),
(2) Date: Dec. 27, 2022

(87) PCT Pub. No.: WO2022/255695
PCT Pub. Date: Dec. 8, 2022

(65) Prior Publication Data
US 2023/0192575 A1    Jun. 22, 2023

(30) Foreign Application Priority Data
Jun. 4, 2021 (KR) ........................ 10-2021-0072734

(51) Int. Cl.
| | |
|---|---|
| *B01J 21/18* | (2006.01) |
| *C07C 7/177* | (2006.01) |
| *B01J 23/46* | (2006.01) |
| *B01J 31/24* | (2006.01) |
| *C07C 29/141* | (2006.01) |
| *C07C 29/84* | (2006.01) |
| *C07C 31/27* | (2006.01) |
| *C07C 45/50* | (2006.01) |
| *C08G 63/16* | (2006.01) |
| *C08G 63/85* | (2006.01) |

(52) U.S. Cl.
CPC ............... *C07C 7/177* (2013.01); *B01J 21/18* (2013.01); *B01J 23/462* (2013.01); *B01J 31/24* (2013.01); *C07C 29/141* (2013.01); *C07C 29/84* (2013.01); *C07C 31/278* (2013.01); *C07C 45/505* (2013.01); *C08G 63/16* (2013.01); *C08G 63/85* (2013.01); *C07C 2603/68* (2017.05)

(58) Field of Classification Search
USPC ........................................................ 528/298
See application file for complete search history.

(56) References Cited

U.S. PATENT DOCUMENTS

| | | | |
|---|---|---|---|
| 6,365,782 B1 | 4/2002 | Nakamura et al. | |
| 10,538,472 B1 | 1/2020 | Chou et al. | |
| 10,767,004 B1 | 9/2020 | Chiu et al. | |
| 2005/0272960 A1 | 12/2005 | Dukat et al. | |
| 2021/0253507 A1 | 8/2021 | Chae et al. | |

FOREIGN PATENT DOCUMENTS

| | | | |
|---|---|---|---|
| JP | 09124524 A | * | 5/1997 |
| JP | H09-124524 | | 5/1997 |
| JP | H11-080068 | | 3/1999 |
| JP | H1180067 A | * | 3/1999 |
| JP | 2001-010999 | | 1/2001 |
| JP | 3784514 B2 | * | 6/2006 |
| KR | 10-1200288 | | 11/2012 |
| KR | 10-2019-0142208 | | 12/2019 |
| KR | 10-2020-0121146 | | 10/2020 |
| KR | 10-2020-0138484 | | 12/2020 |
| WO | WO 2020/164598 | | 8/2020 |

OTHER PUBLICATIONS

JP-3784514-B2 (Year: 2006).*
JPH1180067A (Year: 1999).*
JP-09124524-A (Year: 1997).*
International Search Report and Written Opinion for International (PCT) Patent Application No. PCT/KR2022/007236, dated Aug. 29, 2022, 6 pages.

* cited by examiner

*Primary Examiner* — Terressa Boykin
(74) *Attorney, Agent, or Firm* — Sheridan Ross P.C.

(57) ABSTRACT

Provided are a tricyclodecane dimethanol composition which may be usefully applied to the preparation of a high heat resistant polyester by reducing the content of impurities, and a preparation method thereof.

11 Claims, No Drawings

TRICYCLODECANE DIMETHANOL COMPOSITION AND PREPARATION METHOD OF THE SAME

CROSS-REFERENCE TO RELATED APPLICATION

This application is a national stage application under 35 U.S.C. 371 and claims the benefit of PCT Application No. PCT/KR2022/007236 having an international filing date of 20 May 2022, which designated the United States, and which PCT application claimed the benefit of Korean Patent Application No. 10-2021-0072734, filed on Jun. 4, 2021, the contents of each of which are incorporated herein by reference in their entireties.

TECHNICAL FIELD

Background Art

Tricyclodecane dimethanol (3(4), 8(9)-dihydroxymethyl-tricyclo[5.2.1.0$^{2,6}$]decane, TCDDM) is a material used as a monomer in the preparation of polymers such as polyester, polyacrylate, etc.

Tricyclodecane dimethanol may be prepared by performing hydroformylation of dicyclopentadiene (DCPD) to prepare tricyclodecane dialdehyde (TCDDA), followed by hydrogenation thereof, as disclosed in Korean Patent No. 10-1200288.

TCDDM prepared by such a method is a mixture of various structural isomers and stereoisomers, and a polyester resin prepared using the same is characterized in that its crystallization is difficult. Therefore, it is suitable for use as a coating agent for coating the inner surface of a can, etc. However, TCDDM prepared by the above method may include impurities derived from some raw materials or impurities generated during the preparation process, and thus it is necessary to develop TCDDM with a higher purity and a preparation method capable of preparing the same.

PRIOR ART DOCUMENT

Patent Document 1: Korean Patent No. 10-1200288

DISCLOSURE

Technical Problem

There are provided a tricyclodecane dimethanol composition which may be suitably used in preparing a polyester with high heat resistance and high quality by controlling the content of impurities in the composition, and a preparation method thereof.

Technical Solution

To achieve the above objects, there is provided a tricyclodecane dimethanol composition including
tricyclodecane dimethanol, and
an ether compound represented by the following Chemical Formula 1 in an amount of 1% by weight or less:

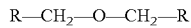   [Formula 1]

in Formula 1,
R's are each independently

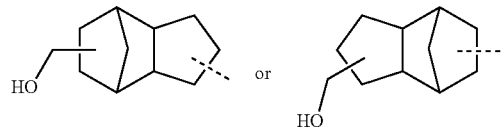

There is also provided a method of preparing the composition, the method including the following steps of ii), iii), iv), and vi), and further including one or more of the following steps of i) and v):
i) purifying dicyclopentadiene by performing the retro Diels-Alder reaction and the Diels-Alder reaction of dicyclopentadiene;
ii) performing a hydroformylation reaction by introducing a catalyst composition including a rhodium-containing catalyst compound and an organophosphorus compound into a reactor, and by adding dropwise dicyclopentadiene under a mixed gas of hydrogen and carbon monoxide;
iii) performing a hydrogenation reaction of the reaction mixture obtained after the step ii) in the presence of a hydrogenation catalyst;
iv) removing the hydrogenation catalyst and the solvent from the reaction mixture obtained after the step iii);
v) performing thin film evaporation of the reaction mixture obtained after the step iv); and
vi) performing vacuum fractional distillation of the reaction mixture obtained after the step iv) or the step v).

Effect of the Invention

A tricyclodecane dimethanol composition of the present invention may be suitably used in preparing a polyester with high thermal stability and high quality by controlling the content of impurities in the composition.

BEST MODE FOR CARRYING OUT THE INVENTION

Hereinafter, the present invention will be described in detail.

Tricyclodecane Dimethanol Composition

A composition of the present invention includes tricyclodecane dimethanol represented by Formula 3, and an ether compound represented by the following Formula 1 in an amount of 1% by weight or less:

R—CH$_2$—O—CH$_2$—R   [Formula 1]

in Formula 1,
R's are each independently

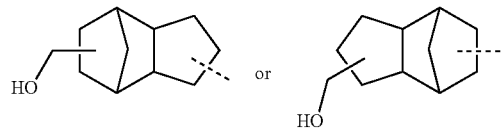

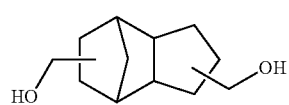   [Formula 3]

Tricyclodecane dimethanol (TCDDM) may be prepared by a preparation method including preparing tricyclodecane dialdehyde (DCDDA) by hydroformylation of dicyclopentadiene (DCPD), and then reducing DCDDA.

In the preparation process, the final product TCDDM may be condensed under high temperature conditions of 150° C. or higher to form a dimer such as Formula 1. Since the dimer has an ether bond, its rotation is possible. For this reason, when the dimer is incorporated into the polymer chain, physical properties of the polymer, such as the glass transition temperature, etc., may be affected.

Accordingly, the TCDDM composition of the present invention includes the dimer in an amount of 1% by weight or less, based on the total weight of the composition such that the composition is suitable for preparing high-quality polymers such as polyester. Preferably, the total weight of the ether compound represented by Formula 1 may be 0.7% by weight or less, 0.5% by weight or less, or 0.3% by weight or less, based on the total weight of the composition, and more preferably, the TCDDM composition may not include the ether compound represented by Formula 1.

Specifically, the ether compound represented by Formula 1 may be one or more selected from the group consisting of the following compounds:

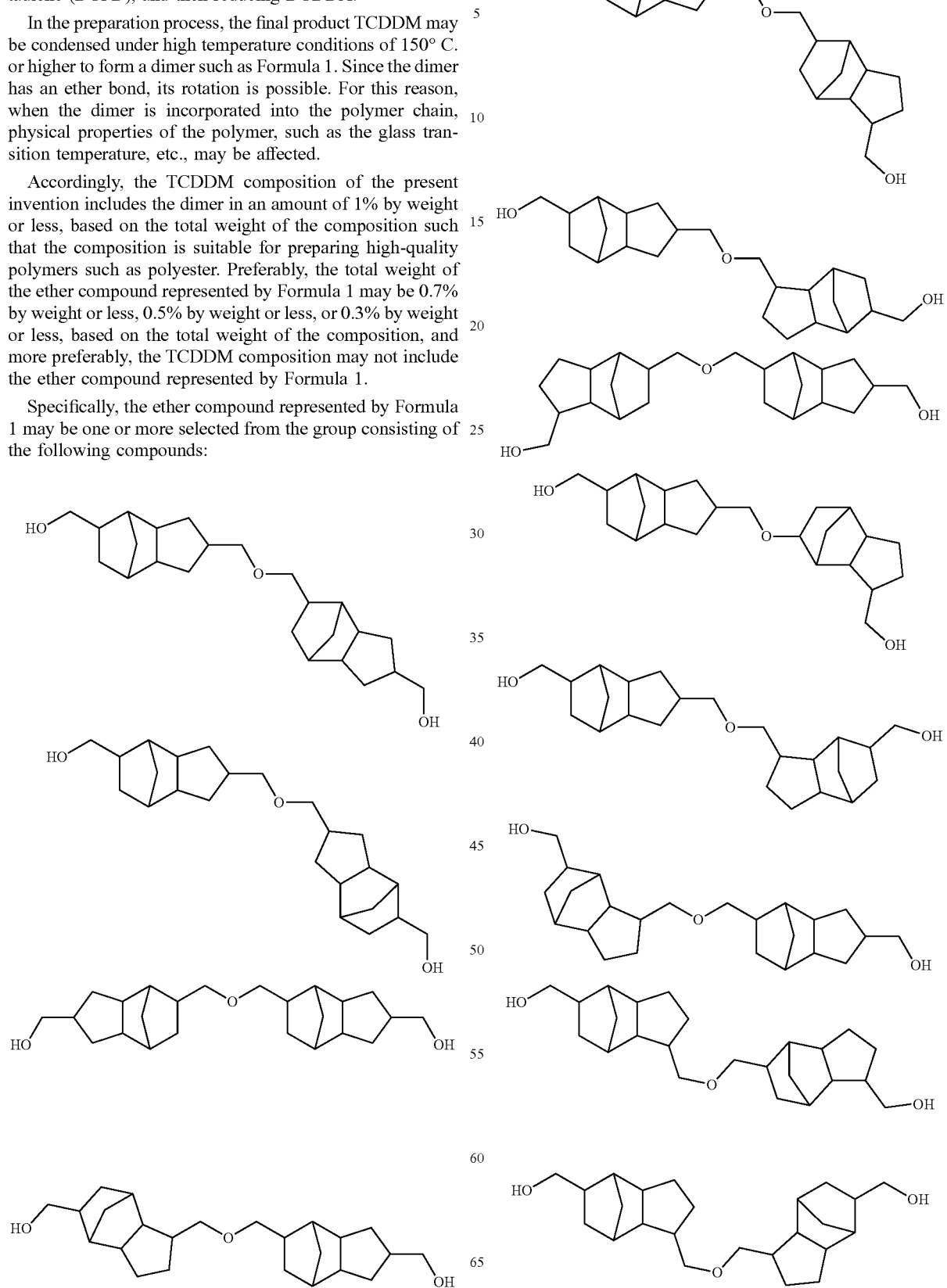

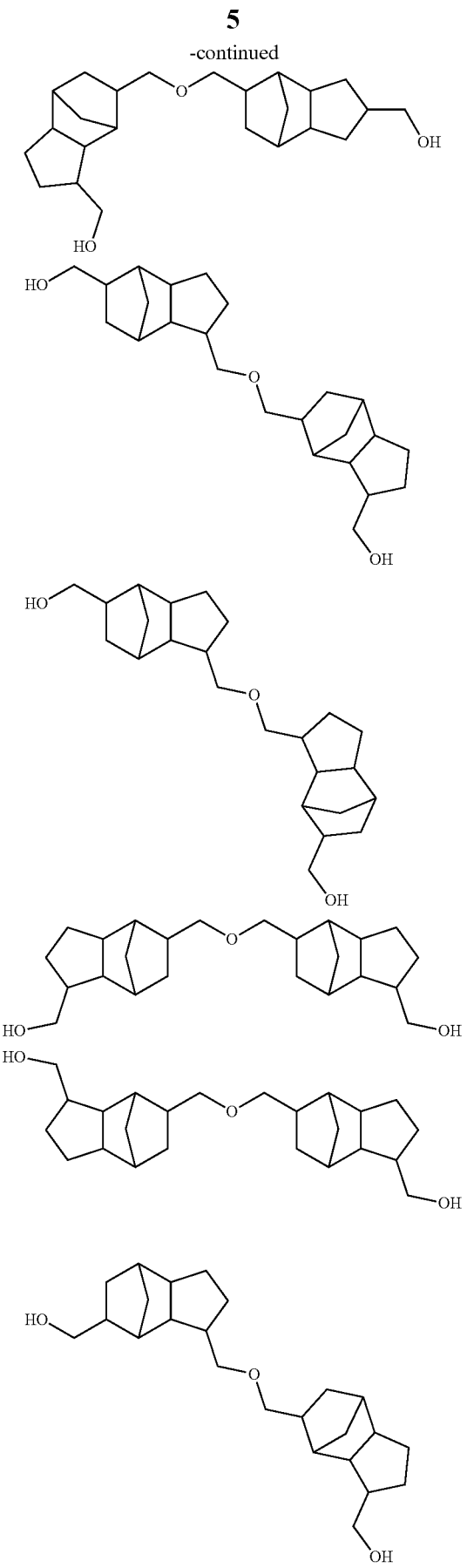
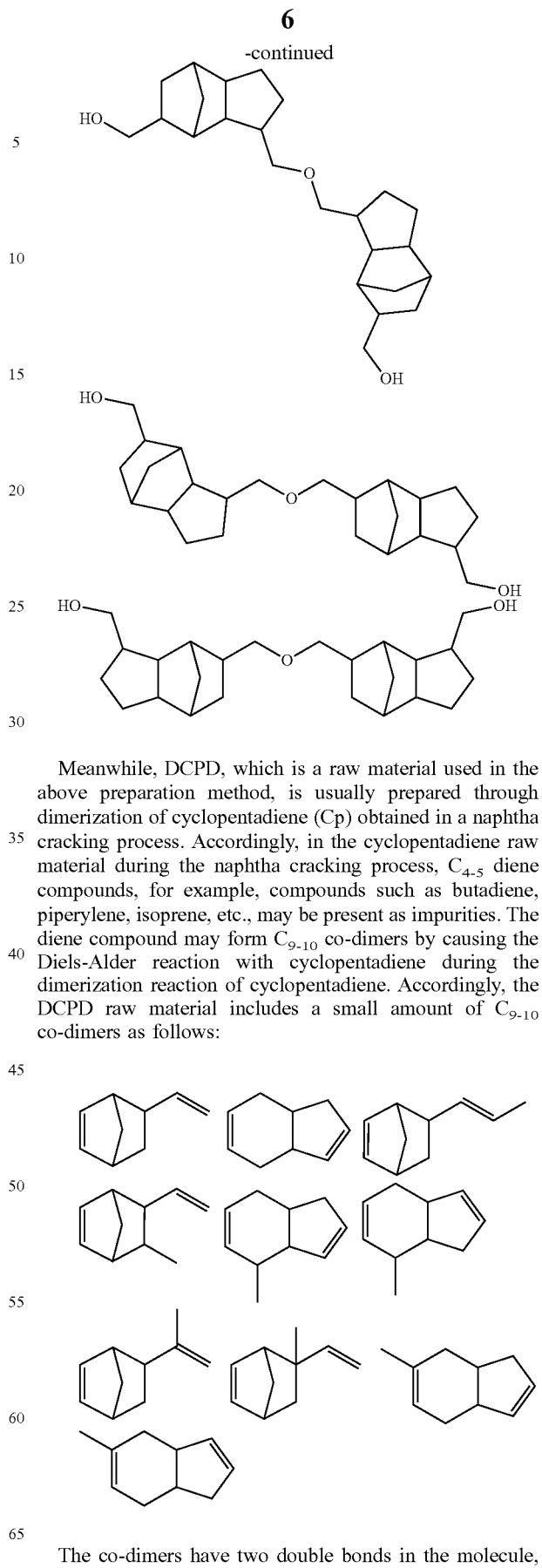

Meanwhile, DCPD, which is a raw material used in the above preparation method, is usually prepared through dimerization of cyclopentadiene (Cp) obtained in a naphtha cracking process. Accordingly, in the cyclopentadiene raw material during the naphtha cracking process, $C_{4-5}$ diene compounds, for example, compounds such as butadiene, piperylene, isoprene, etc., may be present as impurities. The diene compound may form $C_{9-10}$ co-dimers by causing the Diels-Alder reaction with cyclopentadiene during the dimerization reaction of cyclopentadiene. Accordingly, the DCPD raw material includes a small amount of $C_{9-10}$ co-dimers as follows:

The co-dimers have two double bonds in the molecule, like DCPD, and thus a hydroformylation reaction may occur, and through the subsequent hydrogenation reaction, they may be converted to a $C_{11-12}$ diol compound of the following Formula 2-1 or Formula 2-2:

[Formula 2-1]

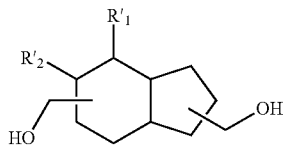

in Formula 2-1, $R'_1$ and $R'_2$ are each independently hydrogen or methyl, provided that none of $R'_1$ and $R'_2$ is methyl,

[Formula 2-2]

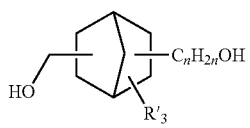

in Formula 2-2, n is 3 or 4, when n is 3, $R'_3$ is hydrogen or methyl, and when n is 4, $R'_3$ is hydrogen.

The TCDDM composition according to one embodiment of the present invention may include the $C_{11-12}$ diol compound in an amount of 3% by weight or less, 2.3% by weight or less, 2% by weight or less, or 1% by weight or less, thereby exhibiting high purity.

The $C_{11-12}$ diol compound may be one or more selected from the group consisting of the following compounds:

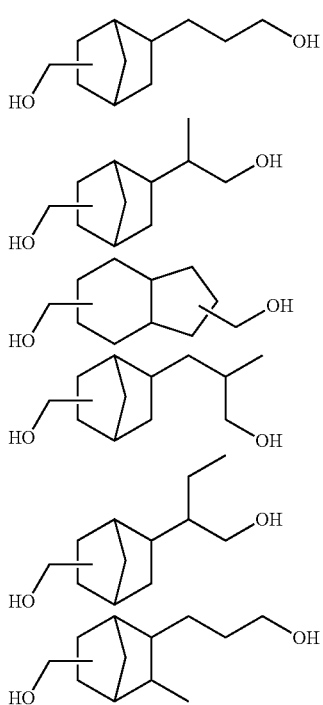

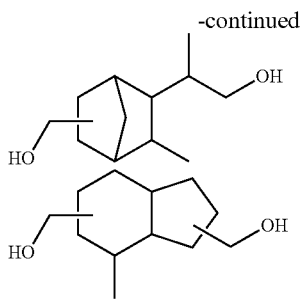

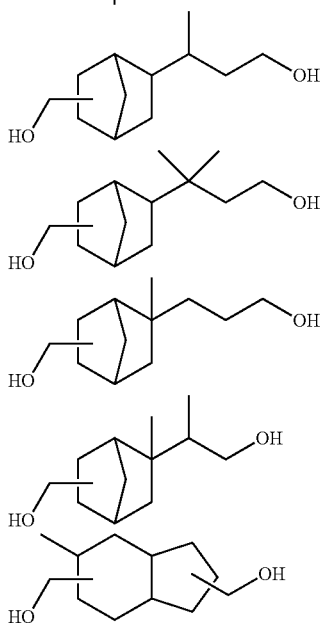

The contents of the TCDDM, ether compound, and $C_{11-12}$ diol compound included in the composition may be identified by analysis of the composition through gas chromatography (GC). The gas chromatography analysis may be performed by, for example, the following method.

The composition is loaded onto a capillary column with a length of 30 m, an inner diameter of 250 μm, and a film thickness of 0.10 μm. An oven is maintained at an initial temperature of 40° C. for 3 min, and then the temperature is increased to 380° C. at an increasing rate of 15° C./min, followed by holding for 5 min. A temperature of the inlet is set to 260° C., and 1.0 μL of the sample is injected. Nitrogen is used as a carrier gas, a flame ionization detector (FID) is used as a detector, and a detector temperature is 260° C.

In the gas chromatography analysis, an elution peak of the TCDDM is observed at a retention time of 13.0 min to 14.0 min, an elution peak of the ether compound is observed at a retention time of 24.0 min to 27.0 min, and an elution peak of the $C_{11-12}$ diol compound is observed at a retention time of 11.5 min to 13.0 min. In this regard, the relative content of each compound may be derived by comparing the area of each peak with respect to the total area of the elution peak (excluding the solvent peak) of the TCDDM composition.

Meanwhile, the composition may include 96% or more, 97% or more, or 99% or more of TCDDM, based on the total weight of the composition, or the composition may consist of 100% of TCDD.

The TCDDM may include a total of three types of structural isomers of 4,8-dihydroxymethyltricyclo[5.2.1.0$^{2,6}$]decane; 3,8-dihydroxymethyltricyclo[5.2.1.0$^{2,6}$]

decane; and 3,9-dihydroxymethyltricyclo[5.2.1.0$^{2,6}$]decane, and a composition ratio thereof is not particularly limited.

Method of Preparing Tricyclodecane Dimethanol Composition

The tricyclodecane dimethanol composition, in which the content of the ether compound represented by Formula 1 is 1% by weight or less, may be prepared by a preparation method including the following steps of ii), iii), iv), and vi), and further including one or more of the following steps of i) and v):

i) purifying dicyclopentadiene by performing the retro Diels-Alder reaction and the Diels-Alder reaction of dicyclopentadiene;

ii) performing a hydroformylation reaction by introducing a catalyst composition including a rhodium-containing catalyst compound and an organophosphorus compound into a reactor, and by adding dropwise dicyclopentadiene under a mixed gas of hydrogen and carbon monoxide;

iii) performing a hydrogenation reaction of the reaction mixture obtained after the step ii) in the presence of a hydrogenation catalyst;

iv) removing the hydrogenation catalyst and the solvent from the reaction mixture obtained after the step iii);

v) performing thin film evaporation of the reaction mixture obtained after the step iv); and vi) performing vacuum fractional distillation of the reaction mixture obtained after the step iv) or the step v).

In other words, the preparation method of the present invention is characterized by essentially including the steps of performing hydroformylation of DCPD, performing hydrogenation of TCDDA obtained from the hydroformylation, and purifying the reaction mixture by vacuum fractional distillation after the hydrogenation, while further including the step of purifying DCPD before the hydroformylation reaction, and/or the step of performing thin film evaporation of the hydrogenation reaction mixture before vacuum fractional distillation.

As described above, the preparation method of the present invention may include one or more of the step of purifying DCPD and the step of purifying the reaction mixture after the hydrogenation reaction by thin film evaporation, thereby obtaining a TCDDM composition with the reduced content of impurities.

Hereinafter, each step of the method of preparing the tricyclodecane dimethanol composition according to one embodiment of the present invention will be described.

Step of Purifying DCPD

In the method of preparing the tricyclodecane dimethanol composition according to one embodiment of the present invention, the step of purifying DCPD by performing the retro Diels-Alder reaction and the Diels-Alder reaction of DCPD may be performed in order to control the impurity content of the raw material DCPD before the hydroformylation reaction (step i).

When the step of purifying DCPD is performed, the TCDDM composition, in which the content of impurities is controlled as described above, may be obtained without the thin film evaporation process of the step v) after the hydrogenation reaction. Alternatively, the TCDDM composition with a higher purity may be prepared by further performing the thin film evaporation process of the step v) to be described later, together with the purification of DCPD.

Specifically, the step of purifying DCPD may include the step of performing the retro Diels-Alder reaction by adding dropwise dicyclopentadiene to a reactor which contains an organic solvent and is maintained at 150° C. to 250° C.; and the step of reacting the cyclopentadiene monomer obtained by the retro Diels-Alder reaction at a temperature of 10° C. to 30° C. to obtain the purified dicyclopentadiene.

The reactor used in the retro Diels-Alder reaction may include a reflux cooling condenser and a distillation head and a receiver connected thereto. Crude DCPD may be injected into the reactor in a dropwise manner. DCPD added dropwise at a high temperature is decomposed into Cp to be vaporized, which is cooled in the distillation head through the reflux cooling condenser, and then collected in the receiver. At this time, DCPD not decomposed during the reaction; and the co-dimers of Cp and $C_{4-5}$ diene contained in the DCPD raw material are condensed by the reflux cooling condenser, and refluxed back to the reactor.

The organic solvent used in the reaction may be diphenylether, triethylene glycol dimethylether, $C_{10-18}$ alkane, $C_{10-18}$ alkene, etc., but is not limited thereto, and any organic solvent having a boiling point of 170° C. to 300° C. may be used without limitation.

In addition, during the retro Diels-Alder reaction, the reaction temperature may be preferably 170° C. to 200° C., and the reaction may be carried out under normal pressure (740 torr to 780 torr).

Pure Cp may be obtained through the retro Diels-Alder reaction, and when it is left at a temperature of 10° C. to 30° C., or 20° C. to 25° C., the Diels-Alder reaction between Cp occurs, and thus it is possible to obtain pure DCPD, in which the content of co-dimers of Cp and $C_{4-5}$ diene is significantly reduced. DCPD purified by this method may have the content of the co-dimers of Cp and $C_{4-5}$ diene of 0.01% to 2.0% or 0.1% to 1.0%.

Step of Performing Hydroformylation Reaction of Dicyclopentadiene

The step ii) is a step of preparing tricyclodecane dialdehyde (TCDDA) by performing hydroformylation of dicyclopentadiene (DCPD).

The catalyst composition used in the hydroformylation reaction includes a rhodium-containing catalyst compound and an organophosphorus compound as a ligand.

The rhodium-containing catalyst compound applicable in the present invention is not particularly limited, as long as it exhibits the hydroformylation activity in the presence of hydrogen and carbon monoxide by forming a complex with the organophosphorus compound. For example, one or more selected from the group consisting of $Rh(acac)(CO)_2$, $Rh_2O_3$, $Rh_4(CO)_{12}$, $Rh_6(CO)_{16}$, $Rh(NO_3)_3$, Rh/Al, and Rh/C may be used. Among them, $Rh(acac)(CO)_2$ may be preferably used.

In the known TCDDA preparation method, the rhodium compound is commonly used in an amount of 70 ppm to 300 ppm in order to increase the conversion rate. However, when it is used at such a high concentration, a separate process is further required to recover the expensive rhodium catalyst, and thus there has been a problem in that the efficiency and economic feasibility of the TCDDA preparation process are reduced. In contrast, in the present invention, since hydroformylation is performed by adding dropwise DCPD in small amounts without adding at once, it is possible to obtain excellent TCDDA conversion rate even with a significantly reduced amount of catalyst. Thus, a separate process of recovering the catalyst is not required, thereby greatly improving the efficiency of the process.

In the present invention, the rhodium-containing catalyst compound is preferably used in the range of 1 ppm to 50 ppm, or 10 ppm to 35 ppm, or 10 ppm to 20 ppm (based on the rhodium element) of the total weight of the reactant dicyclopentadiene. When the content of the rhodium-containing catalyst compound is less than 1 ppm relative to the weight of dicyclopentadiene, the amount of the catalyst is too small and the hydroformylation reaction does not properly occur, and therefore, the conversion rate may decrease. When the rhodium-containing catalyst compound is used in excess of 50 ppm, there may be a problem in that impurities due to side reactions are generated, and a separate process of recovering the catalyst is required. Thus, the above-described effect may not be achieved. For this reason, it is preferable to satisfy the above range.

The rhodium-containing catalyst compound may exhibit catalytic activity by forming a complex with the organophosphorus compound in the organic solvent. In this regard, the applicable organophosphorus compound may be phosphine, phosphite, etc., and preferably, phosphite having a formula of $P(OR^1)(OR^2)(OR^3)$ (wherein $R^1$, $R^2$, and $R^3$ are each independently a substituted or unsubstituted alkyl group or aryl group). Specifically, the organophosphorus compound may be one or more selected from the group consisting of triphenylphosphite, tris(2-t-butylphenyl)phosphite, tris(3-methyl-6-t-butylphenyl)phosphite, tris(3-methoxy-6-t-butylphenyl)phosphite, tris(2,4-di-t-butylphenyl)phosphite, and di(2-t-butylphenyl)phosphite, but is not limited thereto.

The amount of the organophosphorus compound may be adjusted according to the content of rhodium in the catalyst composition. In one embodiment, the organophosphorus compound is used in an amount of 5 moles to 200 moles per 1 mole of rhodium. When the content of the organophosphorus compound satisfies the above range, the content of the ligand per catalyst is sufficient, and thus the hydroformylation reaction may proceed smoothly. Preferably, the organophosphorus compound may be used in an amount of 10 moles or more, 15 moles or more, and 170 moles or less, 150 moles or less, 100 moles or less per 1 mole of rhodium.

The organic solvent applicable to the catalyst composition is not particularly limited, and commonly known inert organic solvents may be appropriately used. Specifically, the organic solvent may include aromatic hydrocarbon compounds, aliphatic hydrocarbon compounds, and alicyclic hydrocarbon compounds.

As the aromatic hydrocarbon compounds, methylbenzenes such as benzene, toluene, xylene, mesitylene, pseudocumene, etc., ethylbenzenes such as ethylbenzene, diethylbenzene, triethylbenzene, etc., propyl benzenes such as isopropylbenzene, 1,3-diisopropyl benzene, 1,4-diisopropyl benzene, etc., and other various alkyl benzenes may also be suitably used. As the aliphatic hydrocarbon compounds, pentane, hexane, heptane, octane, isooctane, dodecane, and decane may be exemplified, but they are not limited thereto, as long as they are a liquid at standard temperature and pressure. As the alicyclic hydrocarbon compounds, cyclohexane, cyclooctane, cyclododecane, decalin, methyl cyclohexane, etc. may be suitably used.

The concentration of the catalyst composition is not particularly limited, but it may be, for example, in the range of 0.01 mM to 5.0 mM, or 0.05 mM to 0.5 mM, based on the rhodium element. When the concentration of the catalyst composition is less than the above range, there may be a problem in that the catalyst reactivity deteriorates due to the excessively low concentration of the catalyst, and when the concentration exceeds the above range, there may be a problem in that the cost of the process increases due to excessive use of the catalyst. Accordingly, the concentration is properly controlled within the above range.

The hydroformylation reaction of DCPD is performed under a mixed gas atmosphere of hydrogen and carbon monoxide, wherein the pressure of the mixed gas is preferably maintained at 20 bar to 150 bar. When the reaction pressure is less than 20 bar, the hydroformylation reaction may not proceed smoothly, and when it exceeds 150 bar, a side reaction may occur to lower the TCDDA yield. More preferably, the pressure of the mixed gas may be 30 bar or more, or 50 bar or more, and 120 bar or less, or 100 bar or less.

In this regard, for smooth progress of the hydroformylation reaction, a volume ratio of hydrogen and carbon monoxide is preferably in the range of 1:10 to 10:1, more preferably, in the range of 1:2 to 2:1.

Under the pressure conditions as described above, the temperature of the hydroformylation reaction step is preferably 50° C. to 100° C., more preferably, 70° C. to 90° C., or 75° C. to 85° C. When the reaction temperature is lower than 50° C., smooth progress of the reaction may be difficult and the yield may decrease. When the reaction temperature is too high by exceeding 100° C., the retro Diels-Alder reaction of DCPD and Cp oligomerization by the Diels-Alder reaction of cyclopentadiene (Cp) generated by the retro Diels-Alder reaction and DCPD may occur.

Meanwhile, in the hydroformylation reaction step of the present invention, the raw material DCPD is added in a dropwise manner to the reactor including the catalyst composition, thereby achieving the excellent conversion rate even with a small amount of the catalyst and minimizing side reactions.

When DCPD is added in a dropwise manner, the concentration of DCPD relative to the concentration of the catalyst composition in the reactor is maintained low, and thus Cp oligomerization that may occur in the presence of a high concentration of DCPD may be suppressed. In addition, since the concentration of DCPD in the reactor may be controlled by controlling the dropwise addition rate, a high conversion rate may be achieved even with relatively small amounts of the catalyst compound and the ligand.

DCPD introduced into the reactor may be prepared in the form of a solution. In this regard, as the organic solvent, an organic solvent applicable to the catalyst composition may be used. The organic solvent used for the catalyst composition and the organic solvent used for the DCPD solution are not necessarily the same as each other, but it is preferable that the same solvent is used, because the reaction may smoothly proceed.

The concentration of the DCPD solution is not particularly limited, and for example, it may be in the range of 0.1 M or more, or 1.0 M to 7.6 M. When the concentration of the DCPD solution is less than the above range, the concentration of the rhodium-containing catalyst compound and the organophosphorus compound in the reactor decreases, as the dropwise addition proceeds, and thus there may be a problem in that the hydroformylation reaction does not proceed smoothly. Accordingly, the concentration is appropriately controlled within the above range.

The dropwise addition rate of DCPD may be controlled according to the concentration of the dicyclopentadiene solution and the capacity of the catalyst composition, and the number of moles of dicyclopentadiene added per minute with respect to 1 mmol of the catalyst (based on the rhodium element) of the catalyst composition is preferably allowed to be 10 mmol to 10,000 mmol, or 100 mmol to 1,000 mmol, or 100 mmol to 500 mmol.

When the dropwise addition rate is too fast by exceeding the above range, it is difficult to achieve the above-mentioned effect due to by-product generation, and when the dropwise addition rate is too slow, the overall reaction rate may become slow, and the process efficiency may be reduced. Accordingly, it is preferable to satisfy the above range.

The hydroformylation reaction time may be appropriately adjusted according to the reaction conditions and the contents of the reactants.

The reaction mixture including TCDDA which is obtained after the hydroformylation reaction undergoes a purification process such as vacuum distillation or thin film evaporation, and then injected for the hydrogenation reaction. For example, the reaction mixture may be subjected to the thin film evaporation under a pressure of 0.1 torr to 10 torr, or 0.1 torr to 1 torr and a temperature of 90° C. to 150° C., or 100° C. to 120° C. to remove the solvent, followed by the hydrogenation reaction.

Step of Performing Hydrogenation Reaction of Tricyclodecane Dialdehyde

Next, the tricyclodecane dialdehyde (TCDDA) mixture prepared through the hydroformylation reaction of the step ii) is hydrogenated in the presence of a catalyst to prepare a tricyclodecane dimethanol (TCDDM) mixture (Step iii).

The hydrogenation reaction may be performed in a solution. As the reaction solvent, a lower alcohol such as methanol, ethanol, isopropanol, etc., water, or a combination thereof may be used. For example, a mixed solvent of water and isopropanol may be used.

As the hydrogenation catalyst, a metal catalyst generally used for hydrogenation of a carbonyl group, for example, a metal catalyst, such as nickel, platinum, palladium, rhodium, ruthenium, copper, chromium, etc., may be used. The metal catalyst may be used in an elemental form, an oxide form, a form of being supported on an inorganic carrier, or a metal complex form. For example, as the hydrogenation catalyst, a ruthenium catalyst (Ru/C) supported on a carbon support may be used.

The amount of the catalyst used may be appropriately adjusted in consideration of the efficiency of the hydrogenation reaction. For example, the hydrogenation catalyst may be used in an amount of 50 ppm to 5000 ppm, or 100 ppm to 500 ppm with respect to the total weight of the reactant tricyclodecane dialdehyde mixture, based on the metal element. When the content of the catalyst is less than 50 ppm, the reaction rate may be too slow, and when the content exceeds 5000 ppm, the preparation cost increases due to excessive use of the catalyst without any particular advantage, and thus it is preferable to satisfy the above range.

The hydrogenation reaction may be performed at a temperature of 80° C. to 250° C. and a pressure of 20 bar to 200 bar, preferably at a temperature of 90° C. to 130° C. and a pressure of 60 bar to 80 bar. When the reaction temperature is lower than 80° C., or the reaction pressure (the pressure of the hydrogen gas) is less than 50 bar, the reaction rate may not be sufficient. When the reaction temperature is higher than 150° C., or the reaction pressure is higher than 200 bar, deactivation of the catalyst may be accelerated, and process costs may increase.

Step of Purifying Reaction Mixture

Next, the reaction mixture obtained after the hydrogenation reaction may be purified to obtain the TCDDM composition.

Specifically, the step of purifying the reaction mixture may further include the step (step iv) of removing the hydrogenation catalyst and the solvent from the reaction mixture obtained after the step iii), and the step (step vi) of performing vacuum fractional distillation of the reaction mixture (step vi), and may further include the step (step v) of performing thin film evaporation of the reaction mixture obtained after the step iv).

Through this purification step, the ether compound of Formula 1 having a high boiling point may be effectively removed without side reactions.

The step of removing the hydrogenation catalyst of the step iv) may be performed by, for example, filtration. The filtration of the reaction mixture may be performed using a vacuum or pressure filtration device commonly used. Filtration conditions are not particularly limited, but filtration may be performed, for example, at a temperature of 0° C. to 150° C. and a pressure of 1 torr to 5 torr.

After the filtration, the solvent is removed from the filtrate through a method such as vacuum distillation, etc. The vacuum distillation may be performed using a device such as a rotary evaporator, etc., and temperature and pressure conditions may be appropriately adjusted according to the used solvent.

After the step iv), thin film evaporation may be optionally performed (step v). Since TCDDM has a high boiling point of 334° C. under atmospheric pressure (760 torr), it has a disadvantage of requiring high temperature conditions when the distillation method is used. However, when the thin film evaporation step is performed, primary purification is possible at a high speed under reduced pressure, and thus the degeneration of TCDDM may be suppressed.

In the thin film evaporation step, acidic or basic high boiling point impurities derived from the hydrogenation catalyst may be effectively removed. The acidic or basic high boiling point impurities are not removed by filtration and may exist in the concentrated reaction mixture after the step iv). When the reaction mixture including these impurities in a concentrated state is subjected to fractional distillation, the dimerization reaction of TCDDM may be accelerated under high-temperature, acidic or basic conditions. Since the boiling point of impurities is high, there is a problem in that long-time distillation is required under high-temperature conditions for purification.

However, when thin film evaporation is performed before fractional distillation, the step vi) may be performed after removing the acidic or basic high boiling point impurities, and therefore, the dimerization reaction of TCDDM is significantly reduced, and the subsequent vacuum distillation of the step vi) may be performed at a relatively low temperature, thereby further suppressing the degeneration of TCDDM.

To achieve the above effect, the thin film evaporation may be performed at a temperature of 100° C. to 200° C. and a pressure of 1 mtorr to 20 mtorr, preferably, at a temperature of 130° C. to 150° C. and a pressure of 10 mtorr to 15 mtorr.

The thin film evaporation may be performed using a thin film evaporator including an evaporator, a condenser, and a decompression means.

The time for which the thin film evaporation step is performed may be appropriately adjusted according to the capacity of the used thin film evaporator, the amount of the reaction mixture, etc. For example, the thin film evaporation step may be performed for 5 seconds or more, 10 minutes or less, preferably, for 5 minutes or less, preferably, 1 minute or less.

Next, after the step iv), or the step v), the obtained reaction mixture is subjected to vacuum fractional distillation to obtain the tricyclodecane dimethanol composition.

The vacuum fractional distillation may be performed, for example, under a pressure of 0.1 torr to 10 torr, or 0.1 torr to 1 torr, and a temperature of 100° C. to 250° C., or 150° C. to 220° C.

When the step v) is performed, vacuum fractional distillation may be performed at a lower temperature than the case where the step v) is not performed. Specifically, vacuum fractional distillation after the step v) may be performed under conditions of a pressure of 0.1 torr to 10 torr, or 0.1 torr to 1 torr and a temperature of 100° C. to 200° C., or 130° C. to 150° C.

The tricyclodecane dimethanol composition prepared by the above-mentioned preparation method, wherein the content of impurities such as the ether compound represented by Formula 1, furthermore, the $C_{11-12}$ diol compound is controlled, may be suitably used in preparing a high-quality polyester with high thermal stability.

Hereinafter, the actions and effects of the present invention will be described in more detail with reference to the specific exemplary examples of the present invention. However, these exemplary examples are provided only for illustrating the present invention, and the scope of the present invention is not defined thereby.

EXAMPLE

Comparative Example 1

(Step 1)

In a 1 L high-pressure reactor, 7.9 mg of $Rh(CO)_2(acac)$ (15 ppm, based on Rh, relative to dicyclopentadiene), and 2 g of tris(2,4-di-tert-butylphenyl)phosphite were dissolved in 100 g of toluene. The mixture was heated to 85° C. while maintaining a pressure of a mixed gas ($CO:H_2$=1:1) at 100 bar. The DCPD solution, in which 10 g of toluene and 210 g of dicyclopentadiene (DCPD) were mixed, was slowly added dropwise to the high-pressure reactor at a rate of 1.3 ml/min (i.e., the amount of DCPD added dropwise per minute with respect to 1 mmol of Rh was 320 mmol) for 3 hours. During dropwise addition of the DCPD solution, the temperature and the pressure inside the high-pressure reactor were maintained at 85° C. and 100 bar, respectively. After completing the dropwise addition of the DCPD solution, the reaction was further allowed under the same temperature and pressure conditions for 1.5 hours.

(Step 2)

The reaction mixture in the step 1 without additional purification was further reacted for 3 hours while heating the mixture to 130° C. and maintaining the pressure of the $CO/H_2$ mixed gas at 100 bar. Then, a sample of the reaction mixture was taken and analyzed by gas chromatography (GC).

(Step 3)

The reaction mixture of the step 2 was concentrated under reduced pressure to remove toluene. The toluene-removed mixture was subjected to thin film evaporation under conditions of 0.2 torr and 130° C. to obtain 281.1 g (yield: 92.0%) of TCDDA(TCD-dialdehyde).

(Step 4)

200 g of TCDDA of the step 3, 100 g of isopropyl alcohol (IPA), 25 g of water, and 3 g of 5% Ru/C (wetted with ca. 50% Water) were mixed and put into a 600 ml high-pressure reactor. The mixture was allowed to react for 4 hours while heating to 130° C. and maintaining a pressure of $H_2$ gas at 70 bar. Then, a sample of the reaction mixture was taken and analyzed by gas chromatography.

(5 Step)

The reaction mixture of the step 4 was filtered to remove Ru/C, and subjected to vacuum distillation under conditions of 100° C./10 torr to remove isopropyl alcohol and water. The TCDDM (TCD-dimethanol) mixture thus obtained was subjected to vacuum fractional distillation under conditions of 150° C. to 220° C. and 0.1 torr to obtain 181 g of a final TCDDM composition.

Example 1

Before hydroformylation, dicyclopentadiene ($C_{9-10}$ co-dimer content of 1-5%) was purified by the following method.

In a 1 L three-neck flask, 400 ml of diphenylether was placed. A thermometer was installed on one side of the three-neck flask and a funnel for dropping DCPD was installed on the other side thereof. A reflux cooling condenser was installed in the center of the flask, and the temperature of the condenser was maintained at 80° C. A distillation head was installed in the reflux cooling condenser. The three-neck flask containing diphenylether was maintained at 200° C. and 1 kg of DCPD was added dropwise at a rate of 10 ml/min using the dropping funnel. The DCPD added dropwise was decomposed into Cp monomer and vaporized. At this time, the decomposed Cp monomer was cooled in the distillation head through the reflux cooling condenser and dropped into a receiver flask. DCPD not decomposed into Cp monomer and Cp-co-dimer were condensed in the reflux cooling condenser and refluxed again into the three-necked flask. 850 g of Cp monomer was obtained by the above method, and left at room temperature (25° C.) for 5 days to be converted into DCPD.

Thereafter, the procedures of the step 1 to the step 5 were performed in the same manner as in Comparative Example 1 to prepare a TCDDM composition.

Example 2

The procedures of the step 1 to the step 4 were performed in the same manner as in Comparative Example 1, and a procedure of the step 5 was performed by the following method.

After Step 4, the reaction mixture was filtered to remove Ru/C, and subjected to vacuum distillation under conditions of 100° C./10 torr to remove isopropyl alcohol and water. The TCDDM mixture thus obtained was subjected to thin film evaporation under conditions of 150° C./10 mtorr. During the thin film evaporation, a thin film evaporator with an evaporation area of 0.04 $m^2$ was used, and the TCDDM mixture was fed at a rate of 15 ml/min. The thin film evaporation step was performed for 15 seconds. The distillate obtained through thin film evaporation was again subjected to vacuum fractional distillation under conditions of 130° C. to 150° C. and 0.1 torr to obtain 181 g of a final TCDDM.

Example 3

DCPD was purified in the same manner as in Example 1, and subsequently, the procedures of the step 1 to step 5 were performed in the same manner as in Example 2 to prepare a TCDDM composition.

[Gas Chromatography (GC) Analysis]

The contents of TCDDM, ether compound, and $C_{11-12}$ diol compound in each of the TCDDM compositions obtained in Examples and Comparative Examples were analyzed by gas chromatography.

Agilent 7890B (GC-FID) as an instrument and DB-5HT (length of 30 m×inner diameter of 250 μm×film thickness of 0.10 μm) model as a column were used, and an oven was maintained at an initial temperature of 40° C. for 3 minutes, and heated to 380° C. at a rate of 15° C./min, and maintained for 5 minutes, followed by analysis. An inlet temperature was 260° C., a detector temperature was 260° C., a flow rate was 1 mL/min, a split ratio was 30:1, a sample injection volume was 1 μl, and a carrier gas was nitrogen.

Detailed analysis conditions are as follows. An elution peak of TCDDM was observed at 13.0 min to 14.0 min, an elution peak of the ether compound was observed at 24.0 min to 27.0 min, and an elution peak of the $C_{11-12}$ diol compound was observed at 11.5 min to 13.0 min, and the content (% by weight) of each compound, based on 100% by weight of the TCDDM composition, was derived from the area of each peak with respect to the total area of the elution peak (excluding the solvent peak) of the TCDDM composition.

<Inlet>
Heater: 260° C., Pressure: 10.7 psi, Total Flow: 33.1 ml/min, Septum Purge Flow: 2 ml/min
Split Ratio: 30:1
<COLUMN>
DB-5HT, 30 m×250 μm×0.10 μm, Agilent
Mode: constant flow, Nominal initial flow: 1.0 mL/min, Average velocity: 20.0 cm/sec
<DETECTOR (FID)>
Temperature: 260° C. (On), Hydrogen flow: 35.0 mL/min (On), Air flow: 350.0 mL/min (On), Makeup flow: 25.0 mL/min (On)
Makeup Gas Type: Nitrogen

TABLE 1

|  | $C_{11-12}$ diol compound (%) | TCDDM (%) | Ether compound (%) |
| --- | --- | --- | --- |
| Comparative Example 1 | 2.31 | 96.62 | 1.07 |
| Example 1 | 0.02 | 99.63 | 0.35 |
| Example 2 | 2.32 | 97.68 | 0.0 |
| Example 3 | 0.01 | 99.99 | 0.0 |

[Preparation of Polyester Resin]

Polyester resins were prepared using each of the TCDDM compositions of Comparative Examples and Examples by the following method.

In a 2000 mL four-neck flask equipped with a thermometer, a condenser, a mantle, a stirrer, and a vacuum pump, 549.0 g of terephthalic acid and 6.3 g of trimellitic anhydride as an acid component, 117.9 g of 2-methyl-1,3-propanediol as an alcohol component and 521.5 g of the TCDDM composition were placed, and tetrabutoxy titanium was added as an esterification catalyst.

When the temperature was slowly raised from room temperature to 240° C. and water or methanol as a by-product flowed out to a theoretical amount, tetrabutoxytitanium was added as a polycondensation catalyst, the temperature was raised to 260° C., and vacuum reaction was carried out for several hours. As a result, as shown in Table 1 below, copolymerized polyester resins having an intrinsic viscosity of 0.40 dL/g to 0.65 dL/g and a number average molecular weight of 17,000 g/mol to 19,000 g/mol were obtained.

Physical properties of the prepared polyester resins were measured by the following methods, and the results are shown in the following Table.

(1) Intrinsic Viscosity (IV)

0.36±0.0002 g of the sample was dissolved in 30 mL of ortho-chlorophenol at 150° C. for 15 minutes, and then the intrinsic viscosity of the sample was measured using a Ubbelohde viscometer in a thermostatic bath at 35° C.

(2) Glass Transition Temperature (Tg)

Using a differential scanning calorimeter (METTLER TOLEDO, DSC 1), about 6 mg to 10 mg of the polyester resin was filled in an aluminum pan, and the polyester resin was heated from room temperature to 280° C. at a rate of 10° C./min (first scan), and annealed at 280° C. for 3 min. Thereafter, the polyester resin was rapidly cooled to room temperature, and then heated again from room temperature to 280° C. at a rate of 10° C./min (second scan) to obtain a DSC curve.

When the polymer undergoes glass transition, the specific heat of the amorphous material increases, and the DSC curve shows a characteristic shift in the endothermic direction. Therefore, the temperature at which the maximum slope of the curve appeared at the point where the DSC curve showed a first step transition during heating was defined as the glass transition temperature (Tg) of the polyester resin.

(3) Number Average Molecular Weight (Mn) and Weight Average Molecular Weight (Mw)

The number average molecular weight and weight average molecular weight of each resin were measured using Tosoh's gel permeation chromatography (GPC) and RI detector.

0.03 g of the resin was dissolved in 3 mL of ortho-chlorophenol at 150° C. for 15 minutes, and then 9 mL of chloroform was added at room temperature to prepare a sample. The sample was injected at a temperature of 40° C. at a flow rate of 0.7 ml/min using 12 ml of ortho-chlorophenol:chloroform=1:3 (v/v) solution as an eluent for measurement. The values of Mw and Mn were derived using a calibration curve formed using polystyrene standards. 9 kinds of polystyrene standards having a molecular weight of 2,000/10,000/30,000/70,000/200,000/700,000/2,000,000/4,000,000/10,000,000 were used.

TABLE 2

| TCDDM composition | Intrinsic viscosity (dl/g) | Glass transition temperature (° C.) | Mn (g/mol) | Mw (g/mol) |
| --- | --- | --- | --- | --- |
| Comparative Example 1 | 0.49 | 68.3 | 17700 | 48000 |
| Example 1 | 0.49 | 90.4 | 17600 | 47900 |
| Example 2 | 0.52 | 85.5 | 17300 | 47900 |
| Example 3 | 0.50 | 93.4 | 18000 | 48300 |

Referring to Table 2, it was confirmed that the polyester resins prepared using the TCDDM compositions of Examples 1 to 3 showed a significantly high glass transition temperature, as compared to that of the polyester resin prepared using the TCDDM composition of Comparative Example 1, indicating excellent heat resistance.

The invention claimed is:

1. A tricyclodecane dimethanol composition comprising: tricyclodecane dimethanol, and
an ether compound represented by Formula 1 in an amount of 1% by weight or less,
wherein Formula 1 is represented by:

$$R_1-CH_2-O-CH_2-R_2,$$

and wherein, in Formula 1, $R_1$ and $R_2$ are each independently selected from the group consisting of:

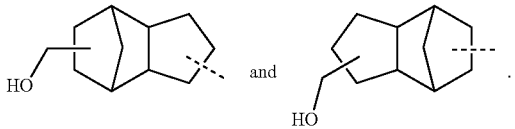

2. The tricyclodecane dimethanol composition of claim 1, wherein a C11-12 diol compound represented by the following Formula 2-1 or Formula 2-2 is included in an amount of 3% by weight or less:

[Formula 2-1]

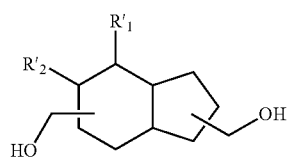

in Formula 2-1,
$R'_1$ and $R'_2$ are each independently hydrogen or methyl, provided that none of $R'_1$ and $R'_2$ is methyl,

[Formula 2-2]

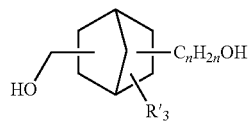

in Formula 2-2,
n is 3 or 4,
when n is 3, $R'_3$ is hydrogen or methyl, and
when n is 4, $R'_3$ is hydrogen.

3. A method of preparing a tricyclodecane dimethanol composition comprising tricyclodecane dimethanol, and
an ether compound represented by Formula 1 in an amount of 1% by weight or less,
the method comprising the following steps of ii), iii), iv), and vi), and further comprising one or more of the following steps of i) and v):
i) purifying dicyclopentadiene by performing a retro Diels-Alder reaction and a Diels-Alder reaction of dicyclopentadiene;
ii) performing a hydroformylation reaction by introducing a catalyst composition including a rhodium-containing catalyst compound and an organophosphorus compound into a reactor, and by adding dropwise dicyclopentadiene under a mixed gas of hydrogen and carbon monoxide;
iii) performing a hydrogenation reaction of the reaction mixture obtained after the step ii) in the presence of a hydrogenation catalyst;
iv) removing the hydrogenation catalyst and the solvent from the reaction mixture obtained after the step iii);
v) performing thin film evaporation of the reaction mixture obtained after the step iv); and
vi) performing vacuum fractional distillation of the reaction mixture obtained after the step iv) or the step v),
wherein Formula 1 is represented by:

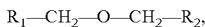

and wherein, in Formula 1, $R_1$ and $R_2$ are each independently selected from the group consisting of:

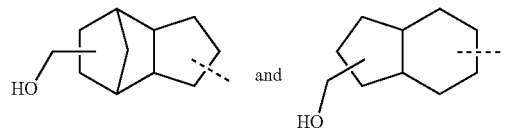

4. The method of claim 3, wherein the step i) includes the step of performing the retro Diels-Alder reaction by adding dropwise dicyclopentadiene to a reactor which contains an organic solvent and is maintained at 150° C. to 250° C.; and the step of reacting the cyclopentadiene monomer obtained by the retro Diels-Alder reaction at a temperature of 10° C. to 30° C. to obtain purified dicyclopentadiene.

5. The method of claim 3, wherein, after the step i), the content of co-dimers of C4-5 diene of dicyclopentadiene and cyclopentadiene is 2% by weight or less.

6. The method of claim 3, wherein, in the step ii), the reaction pressure is 20 bar to 150 bar and the reaction temperature is 50° C. to 100° C.

7. The method of claim 3, wherein the organophosphorus compound is included in an amount of 5 moles to 200 moles per 1 mole of rhodium.

8. The method of claim 3, wherein, in the step ii), the dropwise addition of dicyclopentadiene is performed such that the number of moles of dicyclopentadiene added per minute with respect to 1 mmol of the rhodium element in the catalyst composition is 10 mmol to 10,000 mmol.

9. The method of claim 3, wherein the hydrogenation catalyst of the step iii) is a Ru/C catalyst.

10. The method of claim 3, wherein the hydrogenation reaction of the step iii) is performed at a temperature of 80° C. to 250° C. and a pressure of 20 bar to 200 bar.

11. The method of claim 3, wherein the thin film evaporation of the step v) is performed at a temperature of 100° C. to 200° C. and a pressure of 1 mtorr to 20 mtorr.

* * * * *